Sept. 16, 1952 S. POULSEN Plant Pat. 1,133
ROSE PLANT
Filed Sept. 26, 1951
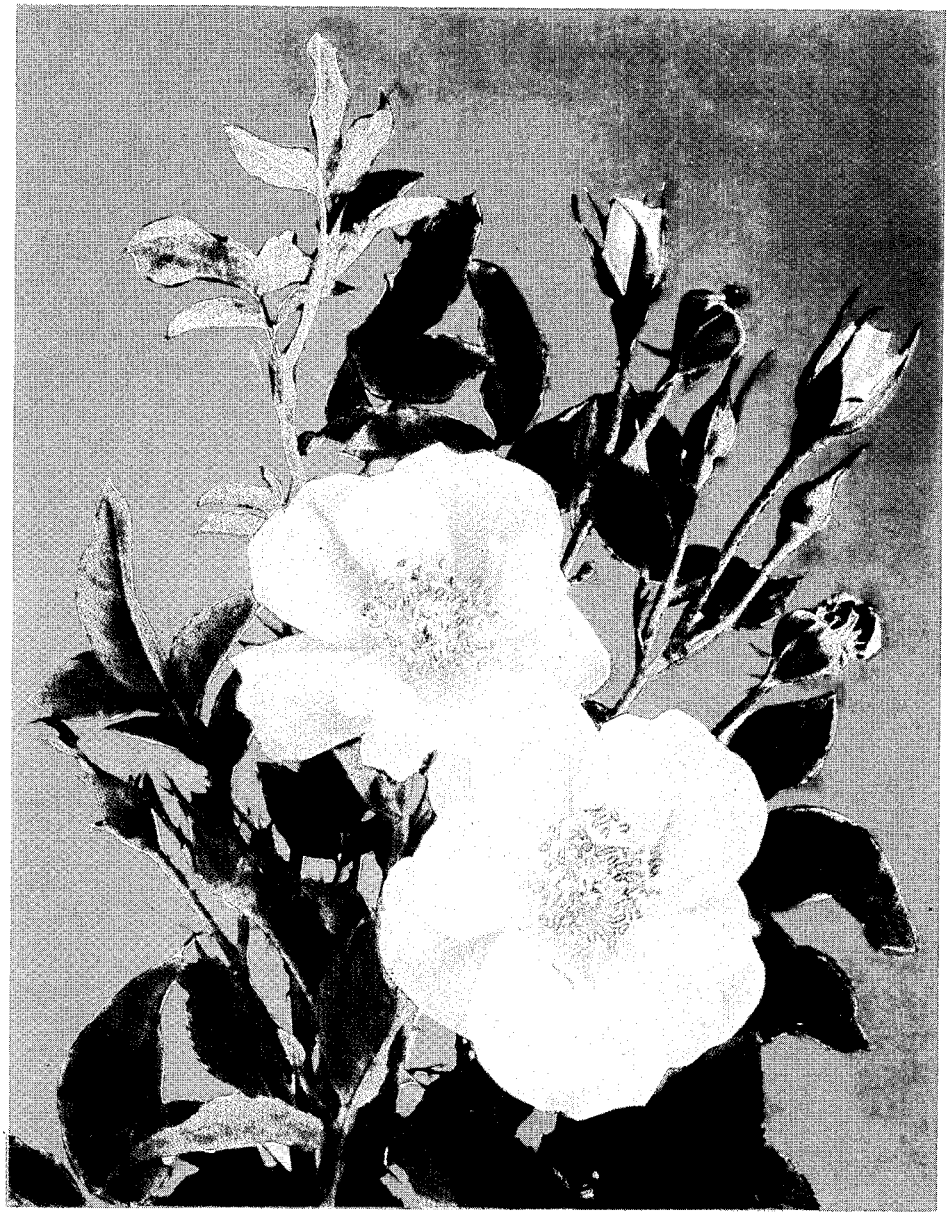
Inventor
Svend Poulsen
By: Robb & Robb
Attorneys Patented Sept. 16, 1952

Plant Pat. 1,133

UNITED STATES PATENT OFFICE 1,133

ROSE PLANT

Svend Poulsen, Copenhagen-Valby, Denmark, assignor to The Conard-Pyle Company, West Grove, Pa., a corporation of Pennsylvania Application September 26, 1951, Serial No. 248,316

1 Claim. (Cl. 47—61)

The present invention relates to a new and distinct variety of rose plant of the hybrid polyantha class, originated by me by crossing the variety "Golden Salmon" (unpatented) × "Julien Potin" (unpatented).

This new variety is distinctly different from its parents and is unlike any other known variety of rose of this class by reason of the fact that it bears relatively large open flowers which are initially yellow in color and resembling big gold medals, but which change in color to shiny white, particularly when sun-struck, so that they have the appearance of silver medals.

A still further outstanding and important characteristic of this new variety is evidenced by the fact that the flowers are borne on top of sizable, sturdy, compact, well-balanced bushes of shapely structure, thereby producing in combination with the colors aforementioned, a unique and distinctive combination of characteristics that enhances the value and desirability of the new variety for cut flowers as well as for garden decoration.

Asexual reproduction of the new variety by budding at West Grove, Pennsylvania, U. S. A., shows that the foregoing characteristics come true to form and are established and transmitted through succeeding propagations.

The accompanying drawing illustrates typical specimens of the flowers and foliage of the new variety in different stages of development.

The following is a detailed description of the new variety, with color terminology in accordance with Ridgway's Color Standards and Nomenclature except where general color terms of ordinary dictionary significance are obvious:

Type: Hardy; bush; outdoor; seedling; for cut flowers and for garden decoration.

Class: Hybrid polyantha.

Breeding: Seedling.

*Seed parent.*—"Golden Salmon."

*Pollen parent.*—"Julien Potin."

Propagation: Holds its distinguishing characteristics through succeeding propagations by budding.

*Flower*

Locality where grown and observed: West Grove, Pennsylvania.

Flowers borne: Several to stem and occasionally singly; in irregular cluster; on normal strength, medium length stems.

Quantity of bloom: Free to abundant outdoors.

Continuity: Continuous.

Fragrance: Moderate; spicy.

Bud:

*Peduncle.*—Medium length; medium weight; erect; medium smoothness; numerous reddish prickles. Color—Cosse Green, Plate V, with a slight bronze tinting.

*Before calyx breaks.*—Size—medium. Form—medium length; ovoid; with foliaceous appendages on the surface of the bud; with foliaceous parts extending beyond the tip of the bud equal to ¼ or more of its length.

*As calyx breaks.*—Color—Greenish Yellow, Plate V, with a Strawberry Pink, Plate I, blush.

*As first petal opens.*—Size—Medium. Form—pointed and ovoid. Color—outside: Pale Lemon Yellow, Plate IV, shading to Picric Yellow, Plate IV; inside: Lemon Chrome, Plate IV, at petal connection, shading to Pale Lemon Yellow, Plate IV, and Picric Yellow, Plate IV.

*Opening.*—Opens up well.

Bloom:

*Size, when fully open.*—Medium; 2½ to 3¼ inches.

*Petalage.*—Semi-double; from 5 to 9 petals; arranged regularly.

*Form.*—Cupped at first; becoming open-cupped; petals being at first loosely cupped inward; becoming later, at maturity, loosely rolled outward.

Petals: Medium thickness; with inside and outside satiny.

*Shape.*—Outer—obovate with apex flat, or occasionally with one notch. Inner—obovate with apex flat, or occasionally with one notch.

This description of a newly opened flower was made from a rose grown outdoors in the month of September, at West Grove, Pennsylvania:

*Color.*—Outer petal—outside surface: Citron yellow, Plate XVI, at base, shading to Barium Yellow, Plate XVI; inside surface: Lemon Chrome, Plate IV, at base, shading to Picric Yellow, Plate IV and Barium Yellow, Plate XVI on outer petal surface. Intermediate petal—Geranium Pink, Plate I, color appears on the margin of one or two of the outer petals at the center of the petal. Inner petal—outside surface: Citron Yellow, Plate XVI, shading to Barium Yellow, Plate XVI; inside surface: Lemon Chrome, Plate IV, at base, shading to Pale Lemon Yellow, Plate IV, and Picric Yellow, Plate IV.

This description was made from a rose that was open for three days outdoors in the month of September, at West Grove, Pennsylvania:

*Color.*—Outer petal—outside surface: Naphthalene Yellow, Plate XVI, at base, shading to white; inside surface: Lemon Yellow, Plate IV, at petal connection, shading to Light Glass Green, Plate XXXI, with most of petal white in color. Inner petal—outside surface: Light Naphthalene Yellow, Plate XVI, shading to white in color; inside surface: Pale Lemon Yellow, Plate IV, at petal connection, shading to a light Naphthalene Yellow, Plate XVI, with most of petal white.

*General color effect.*—Newly opened flower—Picric Yellow, Plate IV, center with outer part of flower Barium Yellow, Plate XVI. Three days open—the flower appears almost white in color with a light Naphthalene Yellow, Plate XVI, in the center around the stamens.

*Behavior.*—Drop off cleanly; fading cream.

*Flower longevity.*—On bush in garden—3 days in July. Cut roses grown outdoors kept at living room temperatures—4 days in July.

*Reproductive organs*

Stamens: Medium to many; arranged regularly about pistils.

Filaments: Most with anthers; short to medium length. Color—Light Coral Red, Plate XIII, at base, and Lemon Chrome, Plate IV, on rest of filament.

Anthers: All open at once; small to medium; seldom an anther fused with a petaloid. Color—Amber Brown, Plate III.

Pollen: Moderately abundant. Color—Capucine Yellow, Plate III.

Pistils: Medium number.

Styles: Fairly even; short to medium; medium thickness; bunched.

Stigma: Color—Oil Yellow, Plate V.

Ovaries: All enclosed in calyx.

Hips: Short; globular; very smooth; walls thick, fleshy. Color—Green.

Sepals: Permanent; medium in length; spear-shaped; recurved.

Seeds: Few; medium size.

*Plant*

Foliage:

*Leaves.*—Compound of 3, 5 or 7 leaflets; moderately abundant; medium size; leathery; glossy.

*Leaflets.*—Shape—ovate with apex acute. Base—round. Margin—simply serrate.

*Color.*—Mature—upper surface: Light Yew Green, Plate XXXI; under surface: Chromium Green, Plate XXXII. Young—upper surface: Parrot Green, Plate VI; under surface: Deep Chrysolite Green, Plate XXXI.

*Rachis.*—Medium heavy. Upper side—grooved; hairy and prickly. Under side—moderately smooth; prickly and with several thorns.

*Stipules.*—Medium length; medium wide; with medium length points turning out at an angle of less than 90°.

*Disease.*—Resistant to mildew and blackspot.

Growth:

*Habit.*—Bushy; upright; branched.

*Growth.*—Free to vigorous.

*Canes.*—Medium heavy.

*Main stems.*—Color—Calla Green, Plate V. Thorns—several; long; straight but occasionally pointed downward; with long, oval base. Prickles—several; color—Brown. Hairs—none observed.

*Branches.*—Color—Lettuce Green, Plate V, with a bronze tinting. Thorns—several; long; straight but occasionally pointed downward; with medium length oval base. Prickles—few. Hairs—none observed.

*New shoots.*—Color—Cosse Green, Plate V, with a bronze tinting. Thorns—many; long; straight but occasionally pointed downward; with medium length oval base. Prickles—few; reddish. Hairs—none observed.

I claim:

A new and distinct variety of rose plant of the hybrid polyantha class, as herein shown and described, characterized as to novelty by its relatively large, open flowers which are initially yellow in color, but which become shiny white, particularly when sun-struck, and by its habit of bearing its flowers on top of sizable, sturdy, compact, well-balanced bushes of shapely structure.

SVEND POULSEN.

No references cited.